United States Patent
Kranck (10) Patent No.: US 11,324,916 B2
(45) Date of Patent: May 10, 2022

(54) DEVICES AND METHODS FOR THE NON-INVASIVE TRANSCUTANEOUS NEUROSTIMULATION OF THE NECK AND EAR VAGUS NERVES VIA ELECTRICAL, MAGNETIC AND HAPTIC STIMULATION

(71) Applicant: Vagus Health Ltd., Cambridge (GB)

(72) Inventor: Gustaf Kranck, Cambridge (GB)

(73) Assignee: Vagus Health Ltd., Cambridge (GB)

( * ) Notice: Subject to any disclaimer, the term of this patent is extended or adjusted under 35 U.S.C. 154(b) by 357 days.

(21) Appl. No.: 16/459,645

(22) Filed: Jul. 2, 2019

(65) Prior Publication Data

US 2020/0001041 A1    Jan. 2, 2020

Related U.S. Application Data

(60) Provisional application No. 62/692,918, filed on Jul. 2, 2018.

(51) Int. Cl.
| | |
|---|---|
| *A61M 21/02* | (2006.01) |
| *A61N 2/00* | (2006.01) |
| *A61N 1/36* | (2006.01) |
| *A61N 2/02* | (2006.01) |
| A61M 21/00 | (2006.01) |

(52) U.S. Cl.
CPC ......... *A61M 21/02* (2013.01); *A61N 1/36025* (2013.01); *A61N 1/36036* (2017.08); *A61N 2/002* (2013.01); *A61N 2/02* (2013.01); *A61M 2021/0022* (2013.01); *A61M 2021/0027* (2013.01); *A61M 2021/0055* (2013.01); *A61M 2205/0216* (2013.01); *A61M 2205/3576* (2013.01); *A61M 2209/088* (2013.01); *A61M 2210/0662* (2013.01); *A61M 2230/04* (2013.01); *A61M 2230/10* (2013.01)

(58) Field of Classification Search
CPC .... A61N 1/36036; A61N 2/002; A61N 2/006; A61N 1/36025; A61N 2/02; A61M 2209/088; A61M 2021/0027; A61M 21/02; A61M 2230/04; A61M 2021/0022; A61M 2021/0072; A61M 2205/332; A61M 2205/3576; A61M 2210/0662; A61M 2021/0055; A61M 2230/10; A61M 2205/0216; A61M 2230/005
See application file for complete search history.

(56) References Cited

U.S. PATENT DOCUMENTS

2007/0067004 A1* 3/2007 Boveja ............... A61N 1/36017
  607/45
2008/0208266 A1  8/2008 Lesser et al.
2010/0292527 A1* 11/2010 Schneider ................ A61N 7/00
  600/15

(Continued)

*Primary Examiner* — Christine H Matthews
*Assistant Examiner* — Joshua Daryl D Lannu
(74) *Attorney, Agent, or Firm* — Laine IP Oy (57) ABSTRACT

A wearable device and method for multimodal stimulation of the vagus nerve having a pair of ear pieces, which are placed at least partially within the concha of an individual. Each ear piece has at least on electric stimulator which provides electric current to the ear of the individual. The wearable device also has a connection which provides stimulation instructions to the stimulators. The method for multimodal simulation also includes iterative biometric measurement and stimulation.

22 Claims, 3 Drawing Sheets

(56) References Cited

U.S. PATENT DOCUMENTS

| | | | |
|---|---|---|---|
| 2013/0085561 A1* | 4/2013 | Mashiach | A61N 1/0526 607/134 |
| 2014/0148637 A1* | 5/2014 | Graft | H04B 1/3838 600/9 |
| 2017/0113057 A1* | 4/2017 | Goodall | A61N 1/37247 |
| 2017/0252562 A1* | 9/2017 | Goldwasser | A61N 1/0456 |

* cited by examiner

DEVICES AND METHODS FOR THE NON-INVASIVE TRANSCUTANEOUS NEUROSTIMULATION OF THE NECK AND EAR VAGUS NERVES VIA ELECTRICAL, MAGNETIC AND HAPTIC STIMULATION

BACKGROUND

Stress is a major health problem in today's society. Humans are constantly trying to find means to relax their brains and alter brain states for the better. At the same time modern society demands increased cognition capacity due to the quickly increasing information flows and complexity of life. The brain has not been able to adapt itself and hence people feel a strong need to find new ways to relax or improve cognition and energy levels. As society is becoming increasingly technology-driven, society is ready and in need of technical solutions for how to control mental states.

The autonomic nervous system is the main nervous system involved in the body's stress response. The vagus nerve a very important part of the autonomic nervous system which enable for instance relaxation. The vagus nerve is also the most important nerve for immune system responses and it is considered to be very important in the treatment of autoimmune diseases such as Crohn's.

Vagus Nerve Stimulation (VNS) is a common medical treatment method for various neurological disorders and diseases such as epilepsy, depression and high blood pressure. The main current VNS method is implanting electrical stimulation electronics that are situated around the vagus nerve at the throat area. These have a separate battery and signal generation unit which is implanted in the chest area. These types of implants are most commonly used for treating epilepsy.

The latest technological development has enabled the use of wireless, very advanced measurement electronics which much better than before can detect subtle changes in the human body's bio signals and specifically the autonomic nervous system of which the vagus nerve is a very important part. This data and latest processing capacities in smartphones and computers have enabled new discoveries and innovations on how to use bio signals and new ways to do neuro-stimulation.

Heart rate variability (HRV) is currently the only widely used method to evaluate the vagal tone or the vagus nerve activity. HRV has a major statistically originating flaw when used in short term measurements. Since the heart beats only on average once per second—the statistical accuracy when measuring only 20 or 30 heartbeats (25 second test), is on average low. There is great demand for quick and reliable new ways to determine the stress level of the heart.

Although previously many kinds of brain or nervous system and vagus nerve stimulation devices have been proposed and is being used, none has this far been able to reach higher than 70% success rates in clinical trials.

The present invention provides for improvements over previous non-invasive vagus nerve stimulation in at least the fact that prior solutions only allows for stimulation at limited locations. When VNS occurs at a location other than the neck or on only one-side of the neck without neuro-feedback and individualized stimulation, it is not directly comparable to invasive VNS in the neck, for which therapeutic results are well-documented. Among other patents and patent applications, non-invasive VNS is sometimes mentioned along with invasive VNS methods, but without addressing the problem of unintentional stimulation of nerves other than the vagus nerve, particularly nerves that cause pain [e.g., US20080208266, entitled System and Method for Treating Nausea and Vomiting by Vagus Nerve Stimulation, to LESSER et al]. Previous devices that used fixed stimulation and do not enable neuro-feedback and hence individualization of the stimulation according to time and person. One reasons that the above existing devices and methods have low success rate is attributed to findings that all individuals have very personal neural networks, hence stimulation has to be individualized and not 'one-fit-all' stimulation protocols as these devices and methods apply.

SUMMARY AND EMBODIMENTS

The present invention provides for methods, apparatus and analytical means to modulate the neural activity of the vagus nerve and central nervous system for the user to improve his or her health, stress and ability to achieve deep sleep. The present invention also provides for means to gather advance analytics and combine data with brainwave recordings and other types of analytical data such as skin galvanic properties in order to provide a better picture of overall health and especially that related to the vagus nerve.

With the aid of the present invention neuro-stimulation may be performed with a non-invasive wearable vagus nerve stimulation device which is using dynamic time-varying electric current and magnetic fields which are applied transcutaneously. These stimulations are applied on at least one of: the throat above the right and left vagus nerves; and on the ear at the surface of each ear's concha.

DETAIL DESCRIPTION

Figure 1:
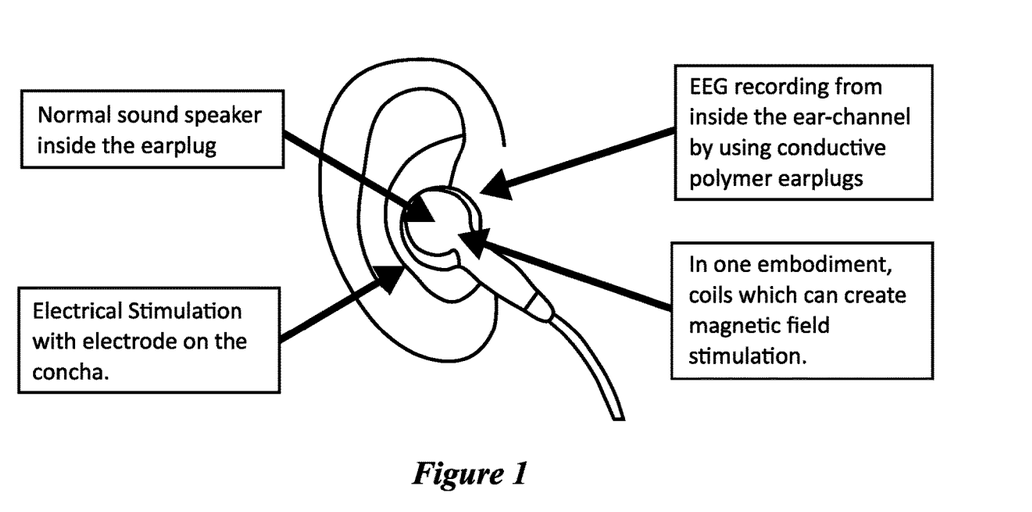
FIG. 1 shows an ear piece stimulator according to at least some embodiments of the present invention

As shown in FIG. 1, at least one embodiment of the present invention provides for an earpiece which is fitted to the ear of an individual. While only one ear piece is illustrated, most embodiments of the present invention utilize a pair of earpieces, one for each ear, in order to provide for more stimulation options. These non-invasive wearable ear pieces provide for vagus nerve stimulation through at least one of: haptic, audio, electrical and magnetic stimulation.

At least some embodiments of the present invention provide for a wearable device for multimodal stimulation of the vagus nerve comprising a pair of ear pieces (similar to that pictured above), and a data connection. As shown, each of the ear pieces is configured to be placed at least partially within the concha of an individual. Furthermore, each ear piece comprises at least an electric stimulator configure to provide electrical current to the ear of the individual. Finally, a data connection is provided so that stimulation instructions and/or energy may be sent to the stimulators.

At least some embodiments of the present invention further comprise at least one energy source conductively connected to the ear pieces.

In at least some embodiments of the present invention the stimulator can provide simultaneous audio signals as voice or music to assist and help the user to achieve better stimulation effect. For example, the device may be used as a sleep aid which provides soothing tones in addition to vagus stimulation to promote deep sleep. Certain sleep aid embodiments provide for audio, haptic and electric stimulation.

In certain embodiments the ear pieces further comprise at least one additional stimulator selected from the group of: haptic, audio and magnetic stimulators. In some embodiments the ear pieces each comprise a haptic, electric and audio stimulator.

According to certain embodiments of the present invention the ear pieces are configured to provide stereo stimulation. That is, the stimulation provided at one ear piece may differ from that provided at the other. This may be accomplished, for example, by control circuitry of the wearable device which is configured to store and deliver a stimulation protocol which includes such stereo stimulation. Stereo stimulation may be implemented by providing differing frequency of stimulation at the left and right ear pieces.

At least some embodiments of the present invention provide for a haptic transducer fixed within the center of an electric stimulation coil.

Certain embodiments of the present invention provide for two stimulation points on the left vagus nerve and two stimulation points on the right vagus nerve. Within at least some embodiments this is achieved by providing two earpieces and two neck pieces. The neck pieces are configured to be placed on opposing sides of the neck of the individual, each neck piece comprising at least one stimulator selected from: haptic, electrical and magnetic stimulators.

Figure 2:
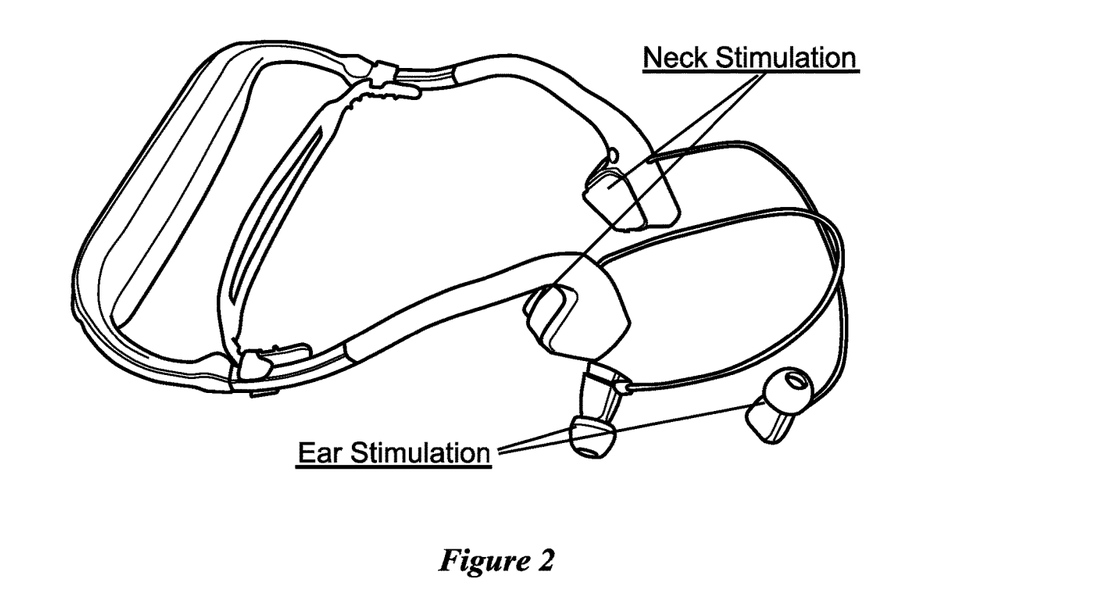
FIG. 2 illustrates an ear and neck stimulator according to certain embodiments of the present invention.

At least one embodiment configured to provide stimulation at both the neck and ears is shown in FIG. 2.

As can be seen in FIG. 2, the wearable device has a pair of neck pieces and a pair of earpieces. Further, according to at least some embodiments, the pictured device comprises an elastically deformable band configured to affix the device to the neck of an individual.

As also illustrated, certain embodiments of the present invention directly connect the ear pieces to the neck pieces in order to provide a more streamlined user experience within having seemingly separate connections to the data connection of the device for each stimulation point.

As pictured at the back of the device above, at least some embodiments of the present invention comprise an energy source for powering the stimulators. Within the same region, certain embodiments also house a memory and control circuitry for storing information and controlling stimulation. For example, the device may be connected to a phone in order to upload a stimulation routing for delivery to the individual when the phone is disconnected.

Embodiments of the present invention incorporating both neck and ear stimulation have been shown to provide better stimulation efficiency not only be increasing the effect per unit of stimulation but also by decreasing the energy needed for the stimulation. Even greater improvements have been seen in stimulation efficiency for those embodiments which provide for stimulation using electrical, magnetic and haptic stimulation on both sides of the neck and ear vagus nerve.

It can be advantages to incorporate at least two different types of stimulators selected from haptic, electric and magnetic stimulators into the neck pieces of the present invention.

One embodiment of the present invention provides for magnetic and haptic stimulation via the neck pieces and electric stimulation via the ear pieces.

Within at least some embodiments of the present invention biometric sensors are integrated into at least one of the earpieces and/or neck pieces.

At least some devices according to the present invention allow for unique simulation programs due to the use of two stimulation points on the left vagus nerve and two points on the right vagus nerve. These stimulation points are separated from each other far enough to enable complex stimulation parameters. As the electrical- and magnetic fields are on both sides of the head, the device can uniquely use a temporally interfering electrical and magnetic fields which influence inner parts of the brain and neck even though the stimulation itself is positioned on the surface of the skin. Temporally interfering electrical and magnetic fields provide increased stimulation effects and targeting of stimulation to certain brain- or nerve areas.

Certain embodiments of the present invention provide the ability to simultaneously stimulate both electrically and magnetically. This simultaneous stimulation enhances and improves the stimulation effect. Certain devices further incorporate using haptic stimulation by the neck area which also increases the effect of the stimulation.

Embodiments of the present invention allow for lower power use and safe wellness-level stimulation powers in order to achieve a large variation of stimulation effects.

As at least some devices according to the present invention can stimulate on both sides of the neck and on 4 distinctively separate points of the vagus nerve, the stimulation programs can use interference patterns whereby for instance the right side is stimulated by a 5000 Hz stimulation wave and the left side with a 5010 Hz stimulation wave. This interference enables the 10 Hz difference to be induced in the vagus nerve and central nervous system parts and improve the stimulation outcome.

At least some wearable devices according to certain embodiments of the present invention also include at least one integrated biometric sensor. Certain embodiments of the present invention also provide for biometric sensors which are connected to or incorporated with the stimulation device. Such biometric sensors include but are not limited to: electrocardiogram (ECG, heart electrical activity), electroencephalography (EEG, brain electrical activity), photometers designed to measure pulse transcutaneously, and other biometric sensors. This sensor may be integrated into an ear piece or neck piece, or may be placed in a separate location on the wearable device.

Within certain stimulation devices according to the present invention configured to provide electrical stimulation, conductive pads or electrodes designed to deliver the electrical stimulation are also configured to record biometric data such as EEG and ECG. Within some embodiments the stimulation device is configured to record EEG from ear pieces and ECG from neck pieces of the stimulation device.

According to at least some embodiments of the present invention the device and electrode design enable the use of both built-in biosignal sensors and separately attached sensors to monitor ECG, EEG and Galvanic Skin response during stimulation. The sensors which are inside or connected separately to the stimulation device receive information or send information either to control circuitry of the device itself or to a separate user device such as a smart phone. Data may be sent to a separate user device via wire (for example using a USB-connection) or wireless signals (Bluetooth or Zigbee radio protocols).

Wearable devices having biometric sensors according to embodiments of the present invention may be configured to deliver stimulation protocols which use bio-signals recorded from the biometric sensors. Such stimulation protocol can use bio-signal recording from the individual to improve the stimulation outcome. At least some stimulation devices according to the present invention may use sensor data recorded from other individuals in order to improve stimulation outcomes. For example, other stimulation devices may deliver and record the outcome of their stimulation protocols and then transmit this outcome data to a central server where the outcome data can be analyzed and forwarded to other stimulation devices.

Certain embodiments of the present invention may utilize music as stimulation signals. Music—as haptic vibration improves the stimulation outcome and improves the attention of the person receiving stimulation.

Stimulators according to at least some embodiments of the present invention are worn on the throat and ears in order to enable the creation of dynamic electrical current, magnetic fields and vibrations on the skin surface by the throat vagus nerve and electrical current and sound in the ear and on the concha which is the vagus nerve area in the ear.

Figure 3:
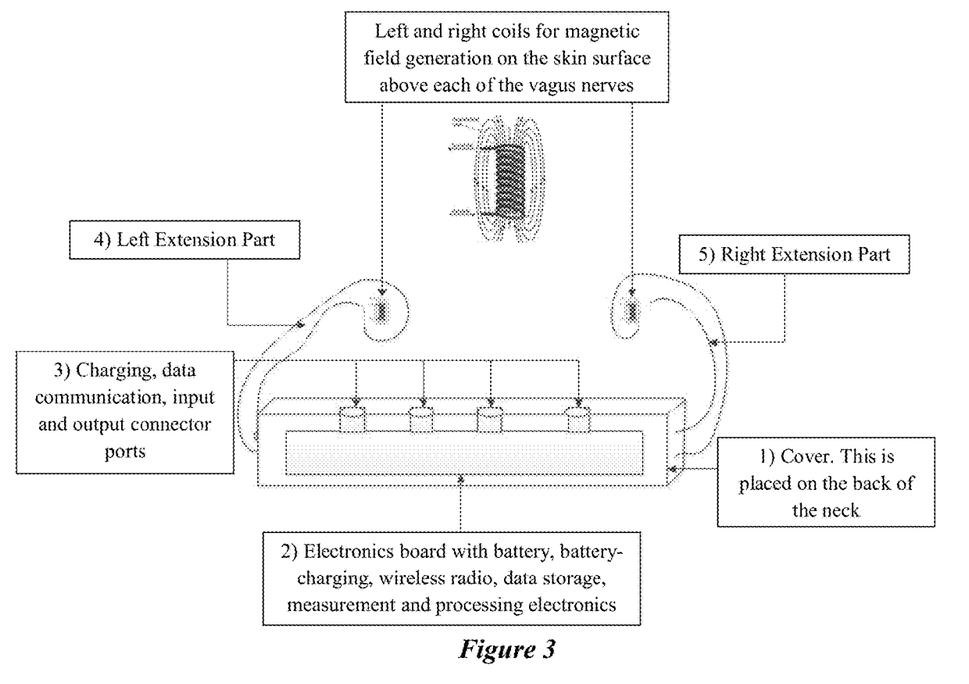
FIG. 3 shows details of an ear and neck stimulator according to at least some embodiments of the present invention.

A neck piece according to at least some embodiments of the present invention is further illustrated within FIG. 3. As can be seen, the neck piece includes a portion to be placed on the back of the neck which includes a battery, charging connection, radio, data storage and measurement and processing electronics or control circuitry.

Figure 4:
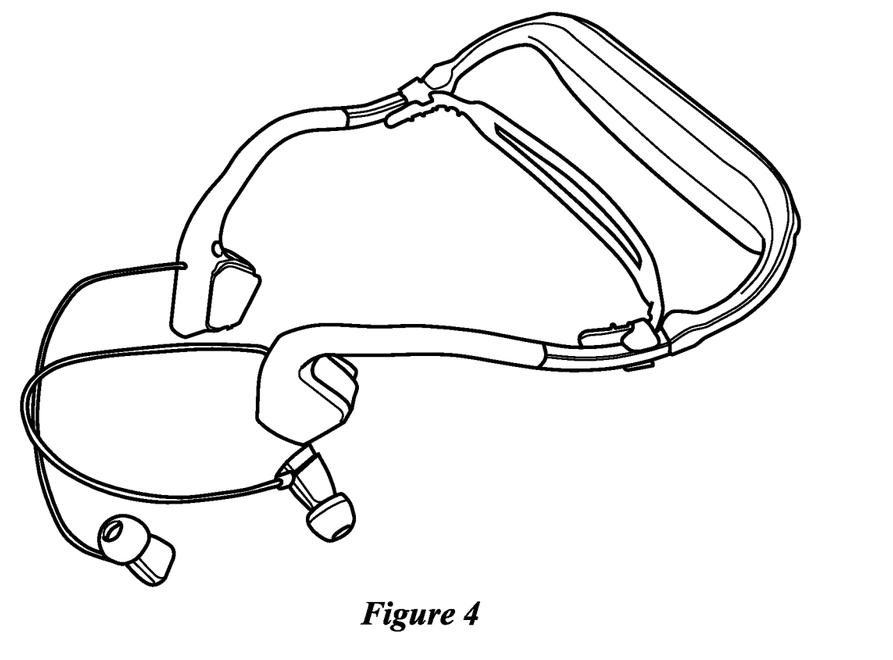
FIG. 4 shows another ear and neck stimulator according to certain embodiments of the present invention.

As can be seen in a further embodiment of the present invention illustrated within FIG. 4, the stimulation device comprises a casing configured to be placed at the back of the neck (portion with white tag at right of picture). The casing houses electronics of the device, including but not limited to an energy source, control circuitry and a data connection and or charging port as previously discussed. Also pictured is an adjustable left and right arm extensions for holding the neck pieces at the appropriate location on the individual. An elastic strap provides for a more secure fit around the neck of the individual. As can be seen, the ear pieces are connected to the neck pieces to provide for a connection of the ear pieces to the electronics. The stimulation device is placed on the neck so that the left and right side coils are place above the left and right throat area above the vagus nerve At least some embodiments provides for left and right coils situated inside the extension arms for the creation of magnetic fields. Certain embodiments include left and right vibration speakers inside the extension arm for the creation of haptic stimulation.

Certain embodiments of the present invention provide for a wearable device having; Signal strength adjustment buttons and/or On/Off buttons.

Still more embodiments include conductive ear plug electrodes for electrical stimulation and/or recording of biosignals.

The stimulation process provided for by at least some embodiments of the present invention is detailed below.

Stimulation

The electric stimulation is generated by sending time varying dynamic electrical currents to the left and right electrode on the extension arm and left and right conductive part of the ear-plug. To achieve the intended stimulation effect, the electric current thereby locally vary both in strength or frequency pattern and the electric current and EMF-fields induced in the body therefore are most usually time varying and dynamically changing between left and right sides. The increased stimulation effect arises in part from this simultaneous but at different strengths and frequencies generated signal patterns that fluctuate between the left and right side vagus nerve. This is a novel feature of this invention.

Within at least some embodiment of the present invention the stimulation is done with frequencies ranging from 0.1 Hz to maximum 10 000 Hz, the main frequency area being between and 5 and 6000 Hz. The stimulation device causes electrical stimulation currents in the body tissue and vagus according to the principle of electromagnetic induction for stimulating live tissue and neurons.

The magnetic fields are generated by sending time varying dynamic electrical currents to the left and right coils in the stimulation device. To achieve the intended stimulation effect, the electric current thereby locally vary to each coil both in strength or frequency pattern and the magnetic fields therefore are most usually time varying and dynamically changing between left and right sides. The increased stimulation effect arises in part from this simultaneous but at different strengths and frequencies generated signal patterns that fluctuate between the left and right side vagus nerve. This is a novel feature of this invention. The stimulation device use's single coils on both left and right side to generate the magnetic fields.

The haptic stimulation is generated by vibration speakers situated in the extension arm. Research show that haptic stimulation at same frequencies as electric and magnetic stimulation, increase the effect of the stimulation. The vibration speakers are also used for sound and music to enhance the user experience and guide the user during the stimulation process.

Certain embodiments provide a stimulation device which has a time-varying magnetic field strength of 0.001 to 3 micro Tesla. At least some embodiments provide for a limit of 3 micro Tesla of magnetic stimulation. As such the device is considered safe for the general public as a wellness device.

With at least some embodiments the device creates a maximum current of 0.5 mA in the body tissues and as such is safe for the user and considered a wellness device as defined by the reference levels and basic restrictions for contact currents in the guidelines by the International Commission of Non-Ionizing Radiation Protection (ICNIRP 2010).

The use of at least two of the three different stimulation modes simultaneously (electric, magnetic and haptic) has not been seen before in vagus stimulation as discussed herein. Certainly not in a wearable device as presently discussed.

At least some embodiments of the present invention provide for a method and device which uses music as stimulation program either without alternation or then mixed with recorded bio signals, machine generated signals or signals generated by artificial intelligence to achieve better stimulation effects.

The method's stimulation programs can be transformed into normal music files and used as such on the stimulation device. Certain embodiments use Waveform Audio File Format or more commonly known as way-format extension.

In one embodiment of the stimulation device innovation, the user experience can be further enhanced when the user at the same time as experiencing magnetic stimulation of the throat vagus nerve, use earphones which are connected to the stimulation device body-part and simultaneously with the stimulation, replay to the ear the same stimulation program or music. These earphones can either be standard earphones with insulation plastic parts or then the inventors designed earphones where the plastic part touching the ear channel is partially electrically conductive or contains a coil generating magnetic fields. The earphones are built so that the ear can with these conductive earphones, receive very low electric impulses or magnetic fields as part of the stimulation and hence activate the part of vagus nerve which is located by the ear channel. This part of the innovation resembles tinnitus vagus nerve ear electric pulse stimulation devices but differs from them since it is only used as an addition to throat vagal nerve magnetic field stimulation by stimulation device. By combining magnetic field stimulation and weak electric pulse stimulation in the ear, the stimulation device stimulation effect is improved. This innovation to simultaneously, with same signal pattern, perform both throat vagus nerve magnetic field stimulation program and same stimulation program or music stimulation to the ear is novel.

Optionally in one embodiment, the measuring stimulation device is stimulation with such signal stimulation programs which can help reduce the blood pressure of the stimulated person. Further the system can learn what stimulation program patterns are best for the user in order to reduce blood pressure and heart stress in general. This system learning can additionally be as feedback measurements from sensors in the stimulation device whereby real-time measurement analyze the degree of relaxation and indirectly blood pressure of the user. This real time measurement can then as a feedback loop adjust the stimulation program to best serve the intended stimulation goal of the user. The system provides an option for such real time feedback adjustment and the user may select such option when starting stimulation.

Optionally, in the stimulation device, the magnetic field generation arrangement includes a plurality of sensors in addition to those two which are on both sides of the throat above the throat vagus nerve, of which some may be on the neck area and some may be situated above the ears. The stimulation program and the electronics can optionally facilitate this plurality of stimulation.

Bio-Signal Sensors Data

As discussed above, certain embodiments of the present invention employ biometric or bio-signal sensors to gather bio-signal sensor data. The devices enable the use of connected or built-in biosensor. The sensors used as connected or built-in are wired or wireless measuring electronics for human bio signals mainly brainwaves (Electroencephalography EEG) and heart rate (electrocardiogram, ECG or EKG).

Such sensor biosignal data may be used in the cloud by the system artificial intelligence to establish what the system perceives to be the optimal individual stimulation program for the user to achieve best effect as he or she has specified in the app when starting the stimulation.

Within at least some embodiments the measurement electronics is measuring bio signal activity by detecting very subtle voltage fluctuations between the sensors skin electrode and pipe electrode. The measured voltage fluctuations are caused by current flows within the neurons of the brain (Electroencephalography EEG), electrical activity of the heart (Electrocardiograph, ECG or EKG), electrical activity of muscles (Electromyography, EMG), electrical conductance of the skin which varies depending on the amount of sweat-induced moisture on the skin (Skin Conductance) or electromagnetic fields in the surrounding of the body.

The sensors in the stimulation device are connected to a user device, such as a phone or use low power wireless signals to transmit data to the user device.

Some example measurement electronics employed in at least some embodiments of the present invention include:

2-electrode (bipolar) signal acquisition, 2000× high gain amplifier

256 Hz or 512 Hz sampling rate, 13 bit effective dynamic range

Built-in 3D (XYZ) accelerometer

Rechargeable LIR1220 button cell, typically >16 hrs use time with full charge

Bio-signal recording of 11+ hours on sensor unit memory module

One silver coated dry electrode touching skin for continuous body-measurement.

One silver pipe electrode as touch electrode for EEG, ECG and EMG and EMF.

It has been shown that sensors connected to the ear-electrode provide an excellent location to measure Brainwaves (EEG). Also sensors in the neck extension part of the stimulation device provide an excellent location to measure electrical heart information and electrocardiogram (ECG)

One important embodiment for the system analytics of sensor data is it can be used to measure various types of Vagal Tone and a Vagus Health Index as specified by the system algorithms.

Methods Enabled by Certain Embodiments

At least some embodiments of the present invention enabled the measurement of stress and health levels. Stimulation devices according to the present invention also equipped with biometric sensors are configured to first record heart rate for 20-60 seconds (ECG), then brainwaves for 20-60 seconds (EEG) and finally also the electromagnetic surroundings by keeping the sensor in the air for 3-10 seconds. This recording is used to determine a baseline stress or health index, for example a Vagal Health Index (VHI). Then a stimulation program is initiated followed by another round of recording biometric data. This allows for a determination of the results of a set of stimulation autonomously.

In one embodiment of a stimulation method according to the present invention an automatic algorithm is changing and adjusting the stimulation program during stimulation. This pattern change is done based on the real-time recording of brainwave signals which are done while the stimulation is ongoing. This type of stimulation program is defined as 'real-time dynamic vagus stimulation'. For example when machine learning has determined the most common brainwave pattern of the user when he or she is alert and energetic, then the dynamic vagus stimulation function is aiming to reach similar brainwave pattern during stimulation. This goal is reached by a scanning pattern in the stimulation program in order to recognize which stimulation pattern is most suitable for reaching the intended end brainwave pattern of the user. This dynamic function can be real time continuous and will be applied for the whole stimulation program In one embodiment of the method when using music as stimulation program, the user can have a different kind of phenomenological conscious experience of the music than with usual musical reproduction devices. The user may also feel various kinds of sensations in the head, throat or body due to the vagus nerve stimulation, which he or she otherwise would not experience. The vagus stimulation can therefore give new types of experiences from music.

At least some stimulation methods can save subjective feedback from the user before and after he or she has used a stimulation program. This feedback can also be as 1 to 5 start rating of the quality of the stimulation experience such as the effectiveness, strength, pleasantness, relaxing effect and/or energizing effect.

Results Achieved

At least some embodiments of the present invention find use as a wellness product. The purpose of stimulation as a wellness product is to help the user to relax, increase vagus nerve activity and vagal tone, improve cognition, become more alert (energetic) or other general and specific wellness effects on the brain and nervous system. The device can also be used as a medical device with therapeutic purposes. As medical sensors in the stimulation device may be used to stimulate the vagus nerve of a patient to treat many conditions, such as: Crohn's disease, Chronic Fatigue, Post-Stroke dysfunction and rehabilitation, improve fertility in general and as part of In-Vitro fertilization treatments, headaches including migraine and cluster headaches, tinnitus, rheumatoid arthritis, dysfunction associated with TNF-alpha in Alzheimer's disease, postoperative cognitive dysfunction, diabetes 1 and 2, Parkinson's disease (including Parkinson's disease dementia) and multiple sclerosis.

Individualized Stimulation

At least some embodiments of the present invention allow for stimulation to be individualized based on user feedback and biosignal measurements. The biosignal measurement can either be done with separate sensors, temporary connected sensors or permanently embedded sensor in the stimulation device. The aim of biosignal measurement is to enable real-time individualization of the stimulation by using artificial intelligence or algorithms, stored locally on the device or remotely, to generate personal stimulation based on user and real-time neuro-feedback sensors data. The creation of stimulation programs can either use individual signals or then combined larger set of different types of biodata from the human body.

The biosignal analytics method has unique features in order to classify and recognize the recorded bio signal recordings and biofeedback. Pattern recognition, machine learning, subjective feedback and unique stress algorithms for both brainwaves (EEG) and heart rate (ECG), determine the usability and classification of recorded bio signals. The measurement and stimulation signal can be adjusted during the stimulation period with feedback from biofeedback measurement which is either real time or non-real time. The method enables social sharing and re-distribution of recorded bio signals and user generated or created stimulation programs.

The stimulation is using use-specific unique stimulation files which are created in the cloud with artificial intelligence in order for it to be personalized and adjusted in real-time primarily based on the biosignal neuro-feedback data provided by the ECG and EEG sensors.

This device and method aim to improve this success rate and achieve better stimulation- and neuro-modulation effect than previous inventions.

At least some stimulation devices according to the present invention allow for storage of personalized stimulation routines. These personalized stimulation routines may be received from a remote location, such as a remote server connected to a user device which is in turn connected to the stimulation device. The personalized stimulation routine may be generated by a remote system's artificial intelligence features based on the users recorded biosignals, personal data and chosen preferences for said stimulation.

At least some embodiments of the present invention, when using real time feedback such as biosignal measurements, automatically adjust the stimulation signals and also create new signals in real time, thereby achieving better stimulation effects.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", i.e. a singular form, throughout this document does not exclude a plurality.

The invention claimed is:

1. A wearable device for multimodal stimulation of a vagus nerve comprising:
   a pair of ear pieces, each being configured to be placed at least partially within a concha of an individual;
   each ear piece comprising at least one electric stimulator configured to provide electric current to an ear of the individual; and
   neck pieces configured to be placed on opposing sides of the neck of the individual, each neck piece comprising at least two different types of stimulators selected from: haptic, electric and magnetic stimulators; and
   a connection configured to provide stimulation instructions to the stimulators.

2. The wearable device of claim 1, wherein each ear piece further comprises at least one additional stimulator selected from: haptic, audio, and magnetic stimulators.

3. The wearable device of claim 1, wherein each ear piece further comprises a haptics stimulator and an audio stimulator.

4. The wearable device of claim 1, further comprising at least one biometric sensor integrated into at least one of the ear pieces and/or neck pieces.

5. The wearable device of claim 4, further comprising memory and control circuitry configured to record biometric sensor data.

6. The wearable device of claim 1, further comprising a memory and control circuitry configured to store and deliver a stimulation routine.

7. The wearable device of claim 1, wherein the connection is a wireless data connection.

8. The wearable device of claim 1, wherein the stimulators of the ear pieces are configured to output stereo stimulation.

9. The wearable device of claim 1, further comprising an energy source.

10. The wearable device of claim 1, wherein the connection also provides energy for stimulation.

11. A method for non-invasively measuring vagus nerve activity and stimulating a vagus nerve comprising the steps of:
    performing a first round of biometric measurement, the round of biometric measurement comprising:
      recording heart rate information via ECG for at least 20 seconds,
      simultaneously or subsequently recording brainwave activity via EEG for at least 20 seconds, and
      recording electromagnetic activity in the surrounding air for at least 3 seconds,
    initiating a stimulation program to supply at least one of: electrical, magnetic, audio or haptic stimulation,
    performing a second round of biometric measurement,
    comparing the first and second rounds of biometric measurement, and
    adjusting the stimulation program based at least in part on the comparison.

12. The method of claim 11, wherein the method is performed using the wearable device of claim 1.

13. The method of claim 11, wherein the stimulation is supplied at or about a vagus nerve of an individual.

14. A wearable device for multimodal stimulation of a vagus nerve comprising:
    a pair of ear pieces, each being configured to be placed at least partially within a concha of an individual;
    each ear piece comprising at least one electric stimulator configured to provide electric current to an ear of the individual, wherein the ear pieces further comprise magnetic stimulators, the magnetic stimulators comprising a coil which surrounds at least a portion of the electric stimulators; and
    a connection configured to provide stimulation instructions to the stimulators.

15. The wearable device of claim 14, wherein each ear piece further comprises at least one additional stimulator selected from: haptic, audio, and magnetic stimulators.

16. The wearable device of claim 14, wherein each ear piece further comprises a haptics stimulator and an audio stimulator.

17. The wearable device of claim 14, further comprising neck pieces configured to be placed on opposing sides of the neck of the individual, each neck piece comprising at least one stimulator selected from: haptic, electric and magnetic stimulators.

18. The wearable device of claim 17, wherein the neck pieces comprise at least two different types of stimulators selected from haptic, electric and magnetic stimulators.

19. The wearable device of claim 17, wherein the neck pieces are held in place by an elastically deformable band.

20. The wearable device of claim 14, further comprising at least one biometric sensor integrated into at least one of the ear pieces.

21. The wearable device of claim 20, further comprising memory and control circuitry configured to record biometric sensor data.

22. The wearable device of claim 14, further comprising a memory and control circuitry configured to store and deliver a stimulation routine.

* * * * *